(12) United States Patent
Hiller et al.

(10) Patent No.: US 6,274,317 B1
(45) Date of Patent: Aug. 14, 2001

(54) AUTOMATED ALLELE CALLER

(75) Inventors: Martha J. Hiller, Waltham; John W. Martin, Cambridge; Alexander N. Parker, Natick; Richard A. Nicoletti, Framingham, all of MA (US); Christopher R. Page, Salem, NH (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/184,448

(22) Filed: Nov. 2, 1998

(51) Int. Cl.⁷ .............................. C12Q 1/68; C12P 19/34; C07H 21/04; G01N 19/00; B01D 57/02
(52) U.S. Cl. .................... 435/6; 435/912; 536/24.31; 536/24.33; 204/450; 204/461; 204/466; 204/600; 204/612; 702/19; 702/20; 382/128; 382/129
(58) Field of Search .................... 435/6, 91.2; 536/24.31, 536/24.33; 204/450, 461, 466, 600, 612; 364/378; 382/129, 128

(56) References Cited

U.S. PATENT DOCUMENTS

| | | | |
|---|---|---|---|
| 5,541,067 | 7/1996 | Perlin | 435/6 |
| 5,580,728 | 12/1996 | Perlin | 435/6 |
| 5,916,747 | * 6/1999 | Gilchrist et al. | 435/6 |

OTHER PUBLICATIONS

Genotyper Software ABI Systems pp. 1–4, 1999.*

Stoughton et al Electrophoresis vol. 18 No. 1 pp. 1–5, 1997.*

"PCR–SSCP: A Simple and Sensitive Method for Detection of Mutations in the Genomic DNA", K. Hayashi, PCR Methods and Applications, 1991, pp. 34–38.

"Methods for Precise Sizing, Automated Binning of Alleles, and Reduction of Error Rates in Large–Scale Genotyping Using Fluorescently Labeled Dinucleotide Markers", S. Ghosh et al, Genome Research, 1997, pp. 165–178.

* cited by examiner

Primary Examiner—Kenneth R. Horlick
Assistant Examiner—Jeffrey Siew
(74) Attorney, Agent, or Firm—Fish & Richardson P.C.

(57) ABSTRACT

An auto allele caller executed in a computer system for identifying alleles from a trace is described. The auto allele caller applies a typical shape of an allele for a marker to the trace to identify potential allele calls that match to the typical shape of the allele at the marker and assigns a quality factor to the allele calls.

28 Claims, 15 Drawing Sheets

AUTOMATED ALLELE CALLER

FIELD OF THE INVENTION

The invention relates to automated allele callers for use in identifying alleles for genetic markers.

BACKGROUND

Genotyping is an important technique in genetic research for mapping a genome and localizing genes that are linked to inherited characteristics such as genetic diseases. In genetic disease studies, for example, a library of genetic markers is screened against DNA samples from affected individuals and their families. Resulting data are analyzed to find chromosomal regions whose transmission from parent to child is correlated with (i.e., linked to) transmission of a particular disease.

The result of screening a single subject marker pair is a "genotype" and comprises one or more so-called alleles that are determined by the subject's DNA sequence at a marker location. Alleles are alternate forms of the DNA sequence at a genetic locus, that is, a position on a chromosome of a gene or other chromosome marker. Persons may be homozygous or heterozygous depending on the number of different alleles they possess for a given marker. Heterozygous persons have two different alleles (one from each parent) for a given marker, whereas homozygous persons inherit the same allele from both parents for a given marker.

As researchers study more complex traits and diseases, the number of genotypes required to detect linkages to such traits and diseases grows significantly. Therefore, performing accurate and high throughput genotyping becomes an important factor for genetic analysis research.

One approach for genotyping uses a large family of microsatellite markers that enable selective amplification. The typical amplification process used is the so-called "polymerase chain reaction" (PCR) technique, which involves the use of a heat stable enzyme to catalyze a synthesis of nucleic acids on pre-existing nucleic acid templates. PCR uses the polymerase enzyme and two base pair primers, one complementary to each strand, at the end of the sequence to be amplified to produce synthesized DNA strands. The synthesized DNA strands serve as templates for the same primer sequence thus permitting successive iterations of primer annealing, strand elongation, and dissociation to produce rapid and highly specific amplification of the desired sequence. The PCR technique is applied to short segments of an individual's chromosome that are known to contain a variable length tandem repeat (i.e., marker). Each possible length corresponds to a distinct allele for the particular marker. The length of the allele is measured by separating the amplified DNA segments by length in lanes on an electrophoretic gel. Because these alleles are transmitted from parent to child, they can be used to trace the inheritance characteristics of chromosomal regions.

Processing an electrophoretic gel is time consuming. To increase throughput, often several markers are multiplexed in each lane of the gel. Markers with overlapping size ranges are tagged with different colored dyes so that their alleles can be distinguished. The same dye can be used for multiple markers, as long as their size ranges do not overlap. A DNA sequencer is used to scan the gel and produce a pixelmap color-coded image in machine-readable format. The pixel information is stored as a file that can be accessed by a gene scanner to produce individual traces. Alleles are determined from these individual traces.

One conventional approach for determining alleles uses a genotyping that presents traces to human "callers" i.e., highly-trained people who visually examine the traces to determine whether or not peaks in particular traces correspond to alleles. Often two different allele callers examine traces in double-blind fashion. If both callers agree that a particular peak or pair of peaks in a trace correspond to alleles, the genotype is "called" or identified. On the other hand, if there is no agreement, the trace may be uncallable.

SUMMARY

The allele calling algorithm assumes that a typical allele morphology can be derived for each marker. This typical allele morphology is used as a target pattern during application of allele calling algorithms to the trace data. The algorithm can train itself to adjust or adapt the typical allele morphology to a given trace. The allele calling algorithm is applied to each trace in sequence. For each trace, possible alleles are tagged with a quality or reasonableness estimate and added to a global list of allele calls and associated tags.

After all possible genotypes for the trace have been examined, a set of heuristic rules are applied to the set of calls to screen out obviously bad allele calls. The heuristic rules exclude bad calls or determine whether the trace should be labeled "uncallable" due to a high degree of uncertainty.

According to the present invention, a method executed in a computer system for identifying alleles from a trace includes applying a typical shape of an allele for a marker to the trace to identify potential allele calls that match to the typical shape of the allele at the marker and assigning a quality factor to the allele calls.

According to a further aspect of the invention, a method executed in a computer system for identifying alleles from trace data includes extracting trace data from a database and preprocessing the trace data to correct for errors in the trace data. The method also includes comparing peaks in the trace data to a typical allele shape to produce potential allele calls and postprocessing the potential allele calls by applying at least one heuristic processing criterion to the potential allele calls to determine whether the potential allele calls should be an allele call.

According to a still further aspect of the invention, a computer program product residing on a computer readable medium for identifying alleles from a trace, comprises instructions for causing a computer to apply a typical shape of an allele for a marker to the trace to identify potential allele calls that match to the typical shape of the allele at the marker and assign a quality factor to the allele calls.

According to a still further aspect of the invention, a computer program product residing on a computer readable medium for identifying alleles from a trace, includes instructions for causing a computer to extract trace data from a database and preprocess the trace data to correct for errors in the trace data. The computer program product also includes instructions to cause the computer to compare peaks in the trace data to a typical allele shape to find potential allele calls, and postprocess potential allele calls by applying at least one heuristic processing criterion to the potential allele calls to determine whether the potential allele calls should be an allele call.

Unless otherwise defined, all technical and scientific terms used herein have the same meaning as commonly understood by one of ordinary skill in the art to which this invention belongs.

Other features and advantages of the invention will be apparent from the following detailed description, and from the claims.

DESCRIPTION

Figure 1:
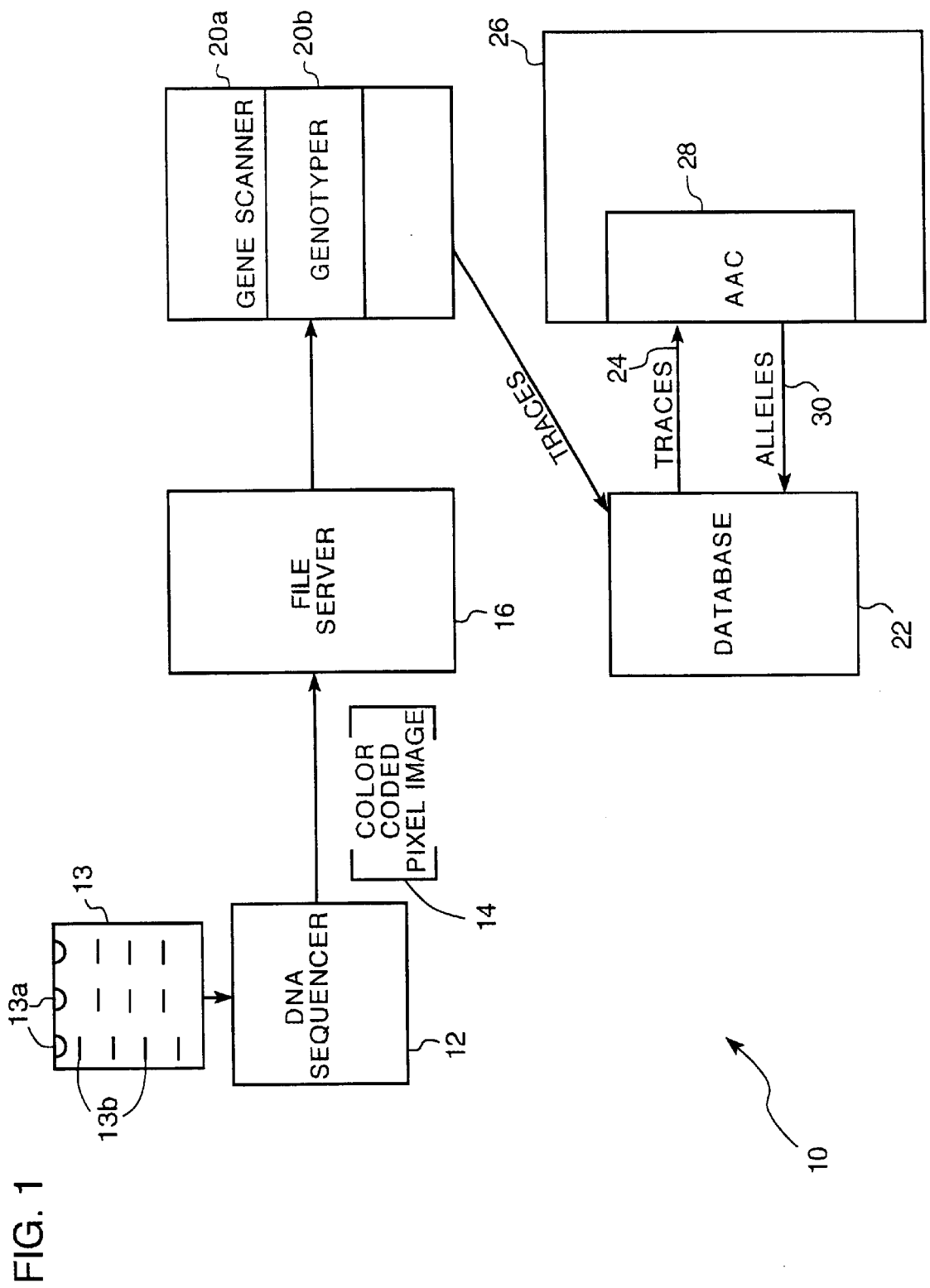
FIG. 1 is a block diagram of a genotyping system including an automated allele caller.

Referring now to FIG. 1, a genotyping system 10 includes an automated DNA sequencer 12 (e.g., ABI system Model 377 from Perkin Elmer, Advanced Biosystems, Inc.) to read an electrophoretic gel (i.e., "gel") 13. The gel 13 carries DNA material in a series of "lanes" 13a. The DNA material can result from an amplification process such as polymerase chain reaction (PCR). The gel 13 in the presence of an electric current separates the PCR amplified DNA material in each of the lanes 13a into a gel image comprised of distinct, spaced bands 13b. When electric current is applied to the electrophoretic gel 13, segments of DNA travel through the gel at a rate inversely proportional to their length. The lanes in the resulting image show the DNA spread out so its length increases monotonically along a time axis.

The DNA sequencer 12 uses a laser to scan the gel and produce a gel image in a machine-readable, digital format. To increase throughput, several markers are multiplexed in each lane of the gel 13. Colors are applied to the markers during the PCR processing. Colors are assigned so that overlapping size ranges have different colors, so that different alleles can be distinguished. Four colors are available. Three of the colors generally carry marker information, whereas, the fourth color carries a size standard that allows mapping between laser scan lines and base pair values. The gel 13 is typically a polyacrylamide gel although other gels can be used. The machine-readable, digital format is a color coded pixel image 14. The pixel image 14 is stored in a file server 16.

A researcher using a genescanning application 20a retrieves the pixel image 14 and produces trace data from the pixel image 14. In the genescanning application 20a, one-dimensional traces are extracted from the center of each lane in the gel image. Each trace signal is a function of signal intensity over time. In the absence of saturation (i.e., the intensity exceeding the dynamic range of the laser scanner of the laser/hardware, a signal is provided having an intensity that is proportional to the quantity of DNA passing in front of the laser at a point in time. The trace data are stored in a database 22. Alternatively, the trace data can be stored on the file server 16.

For each trace, a size standard is used to transform the time domain signal F(t) into a space domain signal f(s) where s is length expressed in base pairs. The trace data are read by an auto allele calling system 26 executing an auto allele caller process 28. Called (i.e., identified) alleles that result from execution of the auto allele caller process 28 are stored in the database 22 or, alternatively, could be stored in another database or file.

Figure 2:
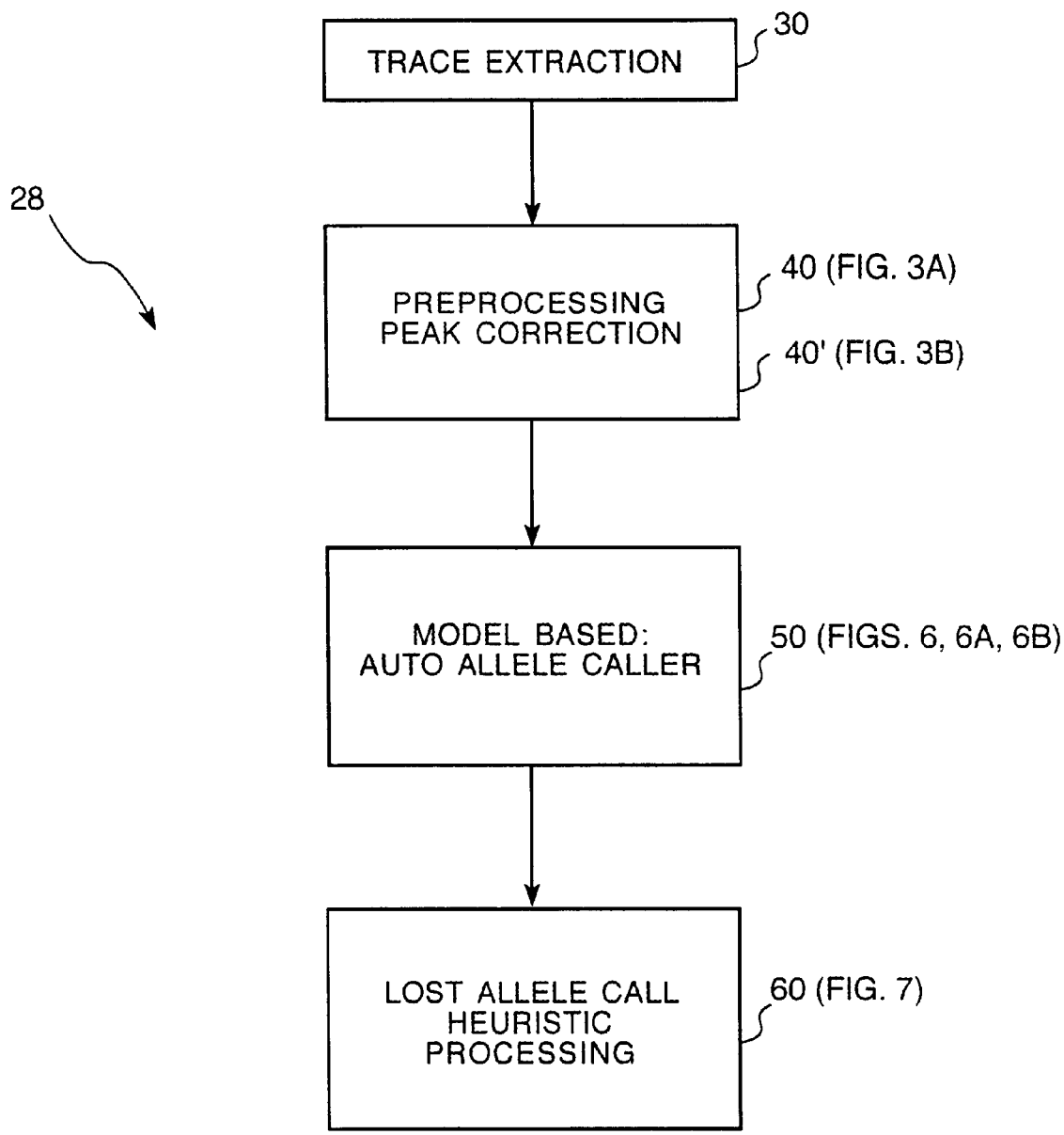
FIG. 2 is a flow chart of a process for automated allele calling in the system of FIG. 1.

Referring now to FIG. 2, the auto allele caller process 28 includes a trace retrieval process 30 that retrieves traces from the database 22. The traces can be processed by either a preprocessing peak correction process 40 (FIG. 3A) or preprocessing peak correction process 40' (FIG. 3B). The preprocessing correction 40 or 40' corrects for split peak and +A errors in raw trace signals. The preprocessing 40', in addition to split peak and +A correction, corrects for so-called "bleedthrough" induced errors. From either the preprocessing peak correction 40 or 40', corrected trace data are fed to a model-based, auto allele caller 50 to produce allele calls that are post-processed using heuristic-based processing 60.

Prior to processing, all experimental data are extracted from the database. The data for an entire DNA sequencing run is extracted and processed as a unit since some preprocessing is global in nature (e.g., spillover, split peak collection, bleedthrough).

Figure 3A:
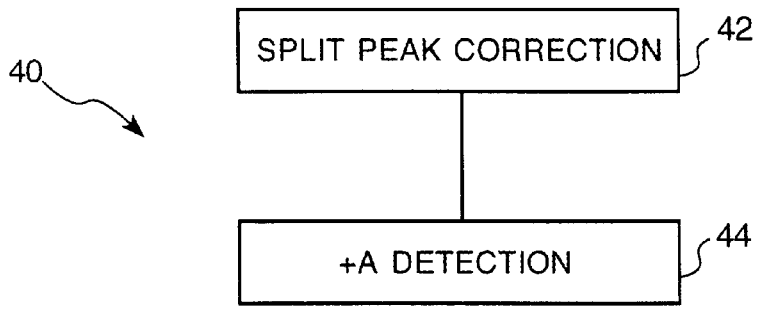
FIGS. 3A and 3B are flow charts of alternative preprocessing techniques for the auto allele caller of FIG. 2.
Figure 3B:
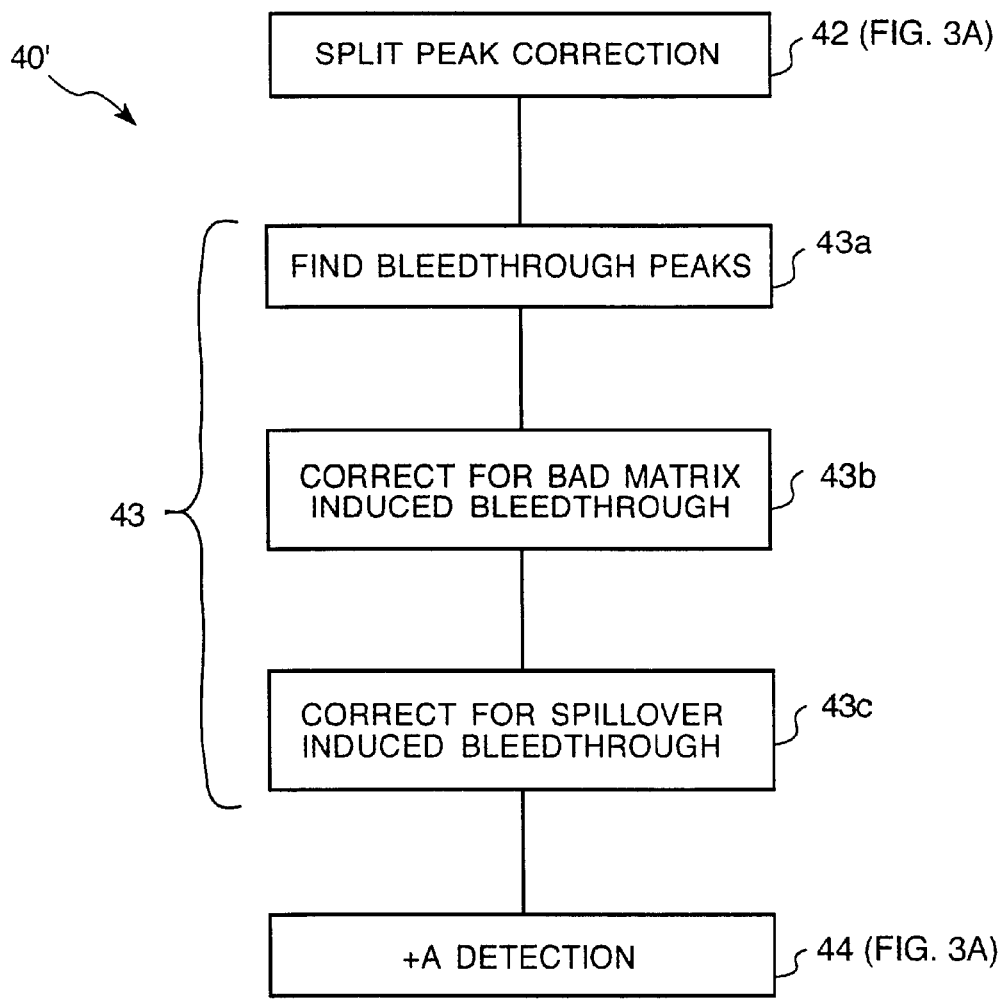

Referring now to FIG. 3A, preprocessing 40 includes split peak correction 42 and +A correction 44 applied to trace data. Errors are introduced during the polymerase chain reaction process. Allele calling can be viewed as a problem of reconstructing an input signal I(s) from trace data where the input signal I(s) is given by Equation 1:

$$I(s)=\delta(s_1)+\delta(s_2) \qquad (1)$$

where the quantity "s" is the length of the DNA fragments between two primers that define the marker, and the input signal I(s) therefore corresponds to the amount of DNA of that length and δ is the "delta function." The input signal I(s) undergoes two major transformations to produce the observed trace output. The first transformation ($a_{pcr}(s)$) occurs during the polymerase chain reaction and the second transformation ($a_{gel}(s)$) occurs when the gel 13 is run through the DNA sequencer 12.

The polymerase chain reaction has two effects on the input signal I(s). One effect is the desired effect, amplification or repeated replication of the original DNA. However, DNA replication also results in a second, undesired effect, that is, copy errors. Because the PCR amplification process used for genotyping is exponential, even a very small rate of copy errors can produce significant signal distortion. Two types of copy errors predominate. The first type is so-called "stutter" where one or more copies of a tandem repeat are missing from the replicated DNA. The second error is a so-called excess adenine or "+A" where an additional adenine base is added to the end of the copy of the DNA from the polymerase chain reaction. In addition, a third type of error sometimes occurs, the so-called "shorty" allele which is caused by poor amplification of an allele.

The input response for polymerase chain reaction impulse ($a_{pcr}(s)$), therefore, contains additional impulses at stutter and +A positions and is given as Equation 2:

$$a_{pcr}(s) = \sum_{k \geq 0} v_k (\delta(s - kR) + r\delta((s - kR) + 1)) \quad (2)$$

where $v_k$ is the volume of DNA transfer to the $k^{th}$ stutter band, R is the tandem repeat size, and r is the ratio of DNA affected by +A error to unaffected DNA. The algorithm assumes extensive variation from one marker to another, and allows for moderate variability from one trace to another for a given marker. Equation 2 assumes that $v_k$ and r are the same for all amplifications within the same PCR reaction. This assumption is generally valid since the values $v_k$ and r are functions of the reaction conditions. Therefore, if the genotype is heterozygous the two impulses will look the same. However, other PCR reactions for the same marker (i.e., genotypes on different traces) will vary, sometimes significantly, and if the individual PCR reaction and the marker are both varied, the overall variation can be extensive.

Within a trace, therefore, an approximation to the polymerase chain reaction output, P(s), is given as in Equation 3:

$$P(s) = c_1 a_{pcr}(s_1) + c_2 a_{pcr}(s_2) \quad (3)$$

Equation 3 assumes a consistent pattern of copy errors within a single PCR reaction. In cases where one allele amplifies much better than the other, (i.e., $c_1$ is very different from $c_2$) the poorly amplified allele is referred to as a "shorty allele."

While the DNA sequencer 12 allows measurement of the DNA, it also transforms the signal, adding baseline noise and signal saturation artifacts. In addition, the gel 13 acts as a low-pass filter. The DNA sequencer 12 and gel 13 are considered to have an impulse response a $a_{gel}(s)$ in the absence of saturation given by:

$$a_{gel}(s) = ce^{-(s/\sigma)^2} + N + \eta \quad (4)$$

where N is baseline noise, $\eta$ is noise from other sources, and the amplitude c and breadth $\sigma$ of the Gaussian distribution $ce^{-(s/\sigma)^2}$ are functions of DNA length (where the area under the Gaussian is constant, but the curve broadens and shortens with increasing length). Thus, a(s) is given as the convolution $a(s) = a_{pcr}(s) * a_{gel}(s)$.

Figure 4A:
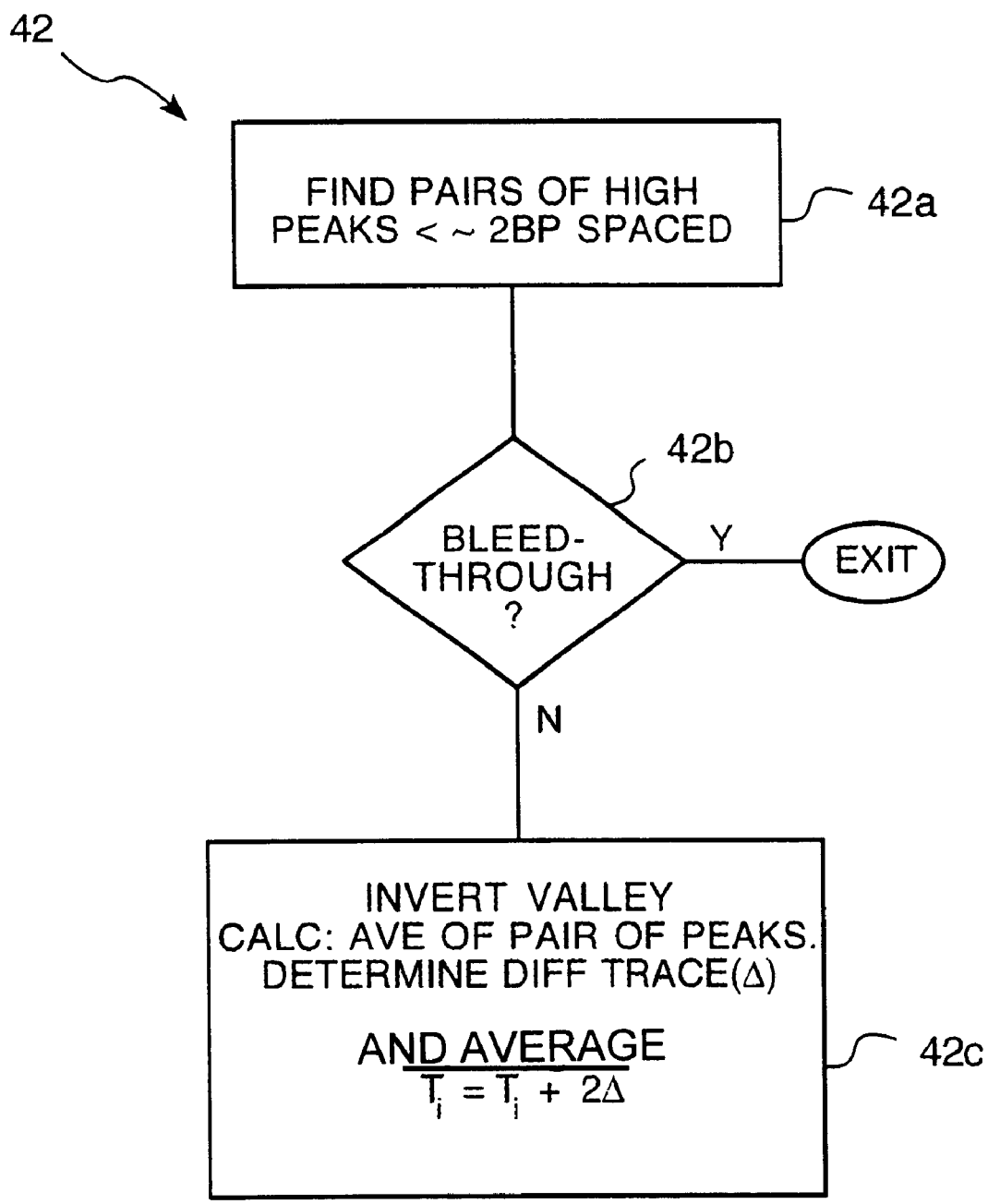
FIG. 4A is a flow chart of a process for correcting for split-peak errors.
Figure 5A:
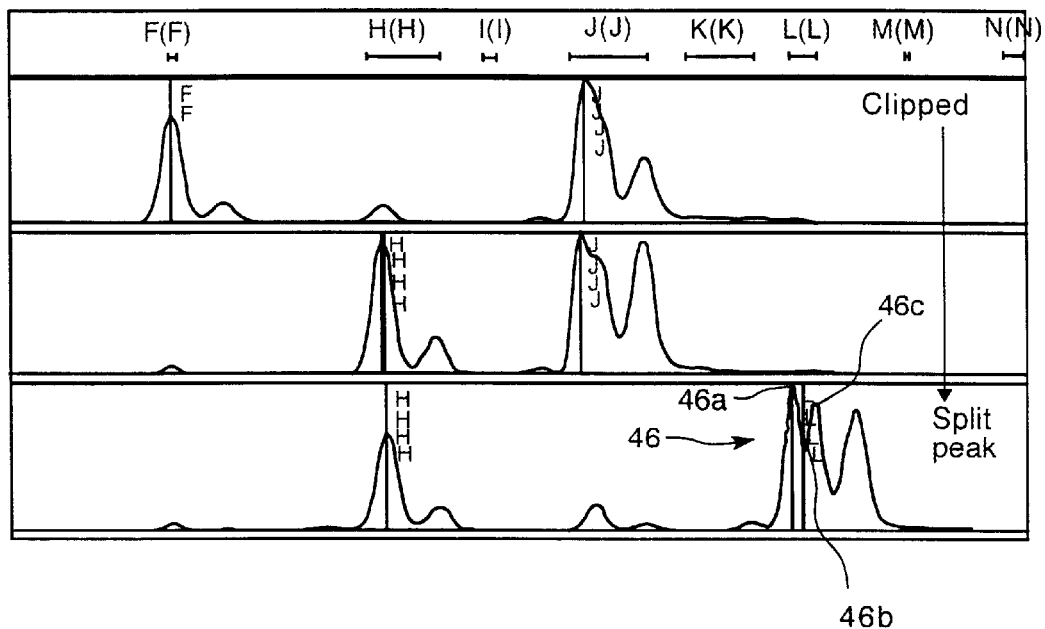
FIGS. 5A–5E are plots of traces of DNA intensity vs. distance (in base-pairs).

Referring now to FIGS. 4A and 5A, the split peak correction 42 (FIG. 4A) removes one of the DNA sequencer 12 artifacts caused by sequence saturation. The split-peak correction finds 42a (FIG. 4A) a pair of peaks having maximum amplitudes greater than the noise level of the system and within a predetermined distance of about two base pairs. As shown in FIG. 5A, a split peak trace 46 has a valley 46b between adjacent peaks 46a, 46c. The split peak correction 42 (FIG. 4A) repairs split peaks by inverting 42c the valley 46b disposed between the pair of adjacent peaks 46a, 46c. The split peak correction 42 determines 42b if bleedthrough occurred in other colors and, if there is no bleedthrough in other colors, assumes that the valley 46b (FIG. 5A) is caused by a split peak error. The split peak correction 42 inverts 42c the valley by finding the average of the maximum values of the two peaks and calculates a difference (on a sample by sample basis) between the value of the trace in the valley ($t_v$) and the average difference. The current value of the trace $t_{ic}$ is given by adding twice this difference ($t_a - t_v$) (sample by sample) to the original value $t_{io}$:

$$t_{ic} = t_{io} + 2(t_a - t_v) \quad (5)$$

This is an approximation to the original peak, but is sufficient to ensure a high success rate in the auto allele calling algorithm described below.

Referring now to FIG. 3B, an alternative preprocessing algorithm includes the split peak correction 42 and +A correction processes 44 of (FIG. 3A), as well as bleedthrough and spillover correction processes 43. The bleedthrough correction processes 43 detects bleedthrough peaks and corrects those peaks for bleedthrough. Bleedthrough correction process 43 detects and corrects (43b) for bad matrix induced bleedthrough by using new bleedthrough/spillover markers and detects and corrects for spillover by using (43c) the new bleedthrough/spillover markers. These bleedthrough corrected peaks are fed to the +A correction 44.

Figure 4B:
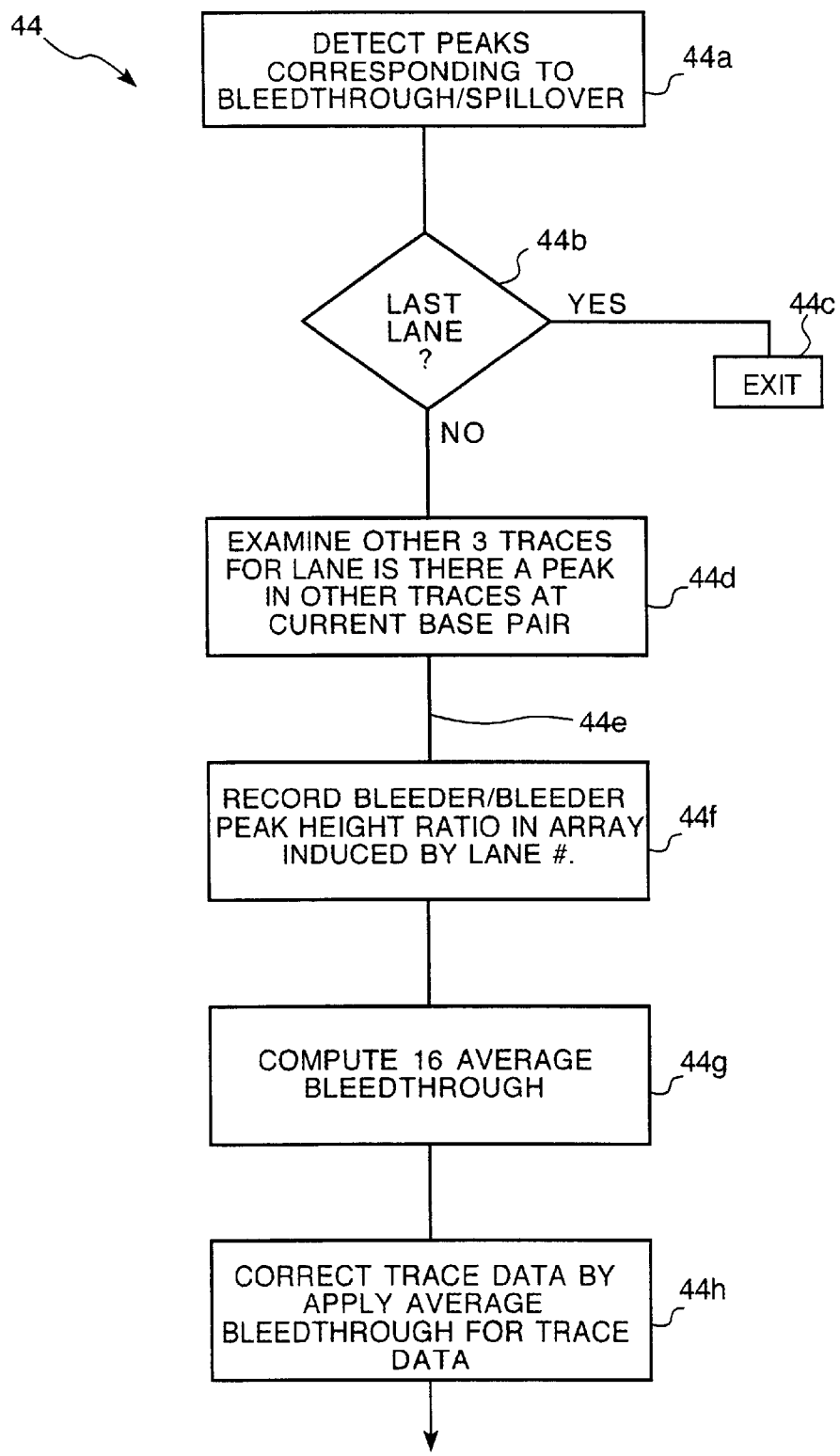
FIG. 4B is a flow chart of a process for correcting for bleedthrough.

Referring now to FIG. 4B, a bleedthrough/spillover correction process 44 is shown. The correction process detects 44a peaks corresponding to bleedthrough or spillover. These are peaks which are markers of known base pair value that are placed at the beginning of each lane of the electrophoretic gel for each trace color. For both bleedthrough and spillover processes 44, 45, these markers serve as a mechanism to calibrate the amount of bleedthrough or spillover which may have occurred. After the peaks corresponding to the bleedthrough/spillover markers have been detected, the data in the lane are processed for each lane in the electrophoretic gel. The process 44 checks 44b if the process has reached the last lane in the gel. If the last lane has been reached, the process exits 44c. Otherwise, if it has not reached the last lane in the gel, the process 44 examines 44e the three other traces for the particular lane to determine whether there is a peak in the other three traces corresponding to the current base pair value. If there is a peak in any one of the other three traces, the process 44 records 44f bleedee/bleeder peak height ratio in an array that is indexed by lane number. The bleedthrough correct algorithm 44 computes 44g the average of bleedthrough for the four colors, that is, for 16 combinations of one color bled into one or more other colors. After the process 44 has computed averages of the 16 combinations, the process 44 corrects 44b the trace data by applying, (i.e., subtracting) the average of the bleedthrough calculated in 44g to the trace data. The resulting trace data corresponds to trace data that is corrected for bleedthrough.

Figure 4C:
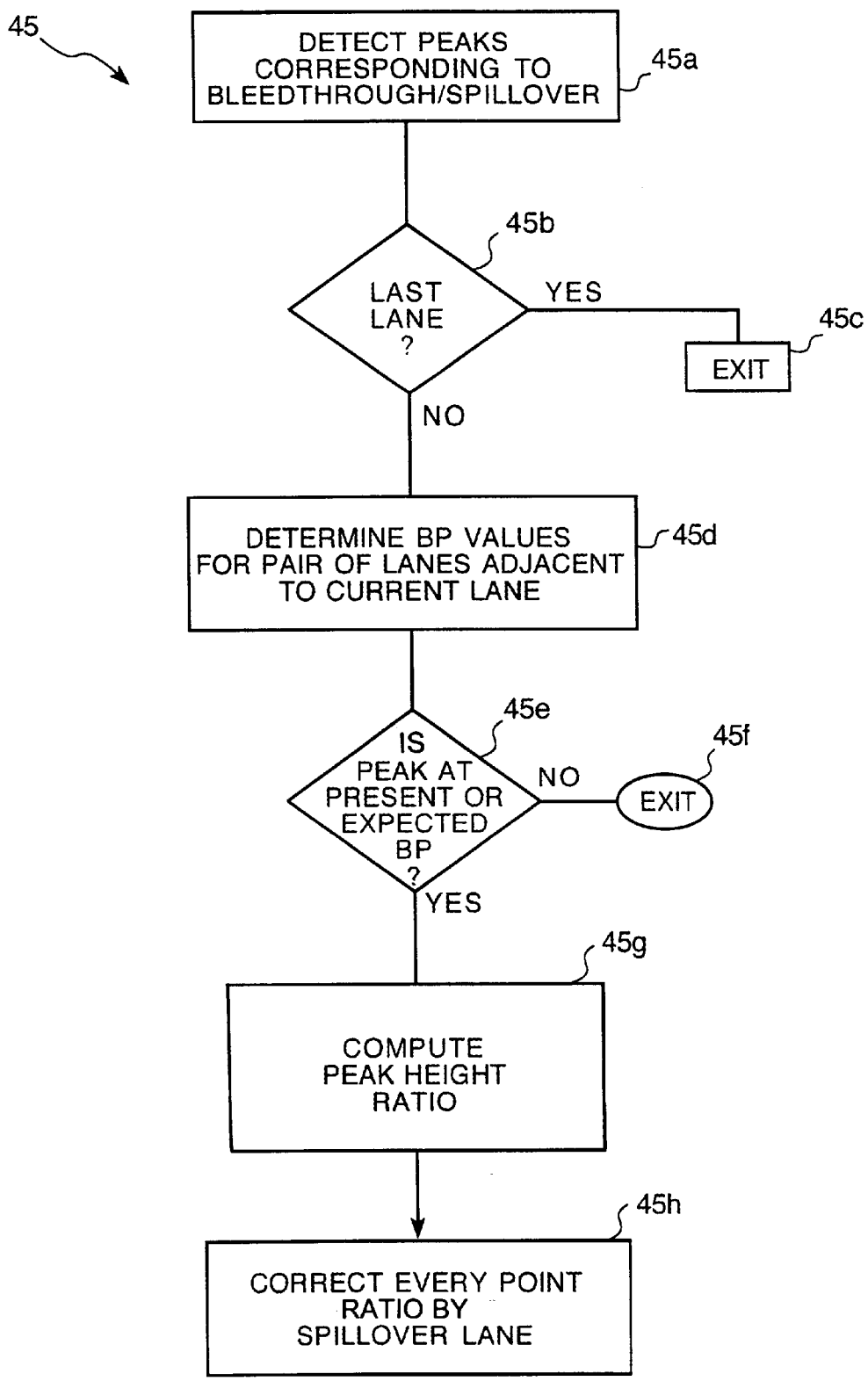
FIG. 4C is a flow chart of a process for correcting for spillover.

Referring now to FIG. 4C, a spillover correction process 45 detects 45a peaks corresponding to bleedthrough and spillover. The process 45 checks 45b if the process 45 has reached the last lane in electrophoretic gel. If it has reached the last lane, it exits 45c. Otherwise, the process 45 determines 45d a base pair value for a pair of lanes that are adjacent to a current lane. The algorithm checks 45e if a peak is present in the current lane at either of the base pair values of the pair of adjacent lanes. If a peak is present in either one or both of these adjacent lanes, spillover has occurred from the adjacent lanes into the current lane. The process 45 computes 45g a peak height ratio for each instance of such spillover and will apply (i.e., multiply) the ratio to correct 45h every point in the spillover lane by an amount corresponding to the ratio. If there is no peak present at either base pair, the process exits at 45f.

Figure 6:
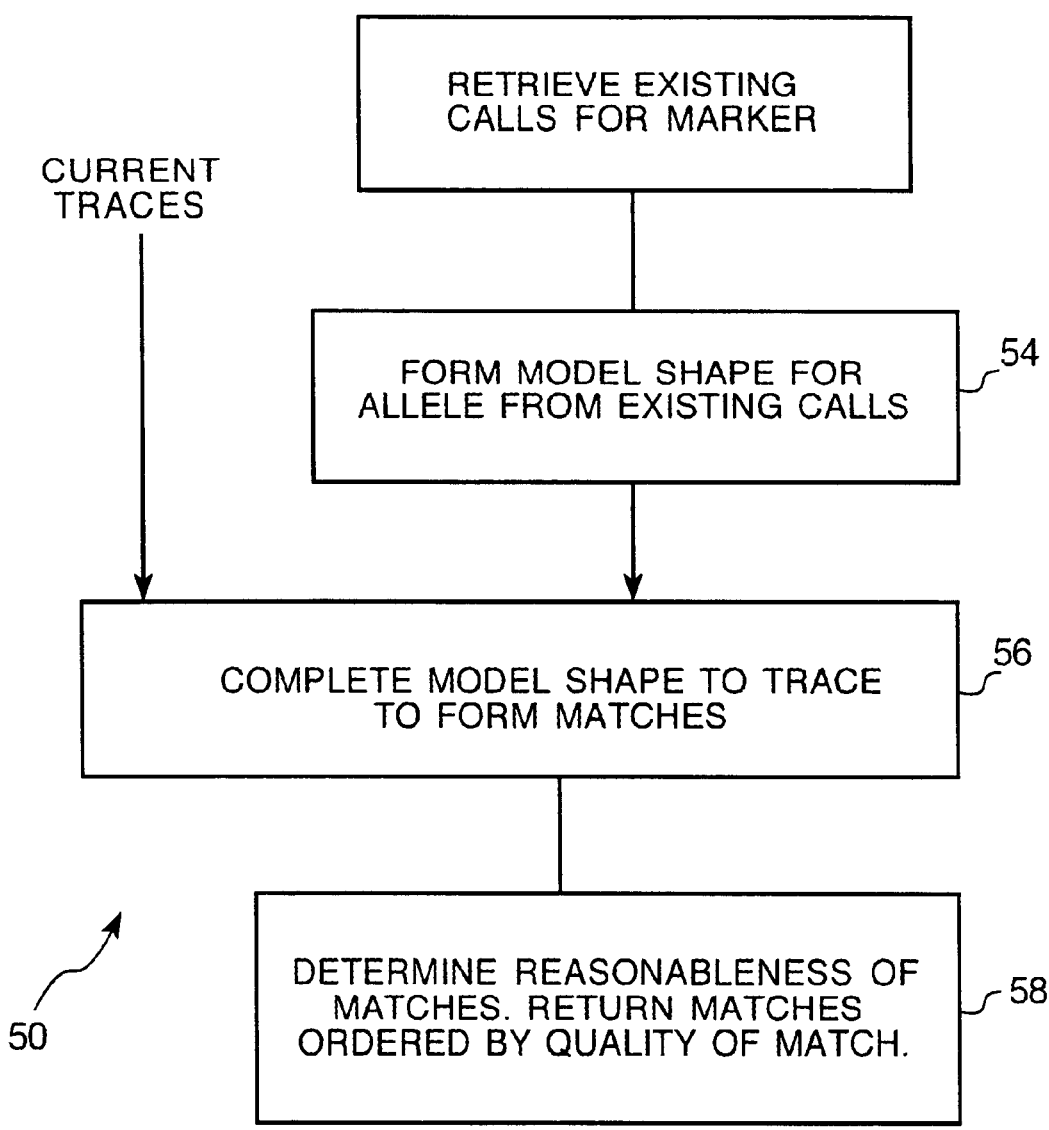
FIG. 6 is a flow chart of a model-based auto allele caller.

Referring now to FIG. 6, preprocessed trace data are fed to the model-based auto allele caller 50 (FIG. 2). The auto allele caller 50 retrieves 52 from the trace database 22 existing calls that have been previously made on the same marker. These calls are calls that have been made by a human caller(s) or another calling algorithm. From the existing calls, the auto allele caller 50 determines 54 a model-shape or typical morphology "τ" of an allele expected for a particular marker. The auto allele caller 50 compares 56 the typical or model shape to a current trace to form matches. The reasonableness of each of the matches is determined 58 and a quality tag is assigned to each match. The auto allele caller 50 returns matches ordered by the quality of match characteristics.

The auto allele caller 50 forms 54 the model trace from a predetermined number of existing allele calls that are retrieved from database 22 and averaged together to provide a typical or model shape for an allele at that marker.

Figure 5B:
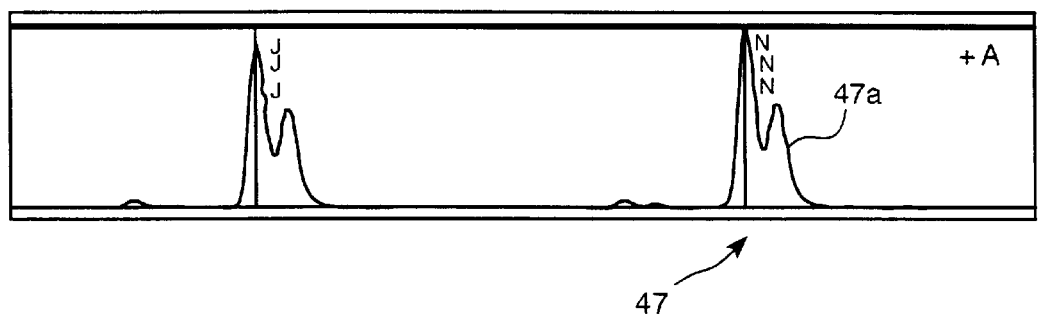

The +A detection is used to ascertain whether a particular trace includes a +A pattern. As shown in FIG. 5B, an +A peak 47 is a "shadow" peak 47a that appears one base pair (IBP) after the primary peak. Dinucleotide markers are very susceptible to +A errors. If a +A peak is detected, the auto allele caller process modifies the typical or model shape to include a +A peak after each primary peak.

Figure 5C:
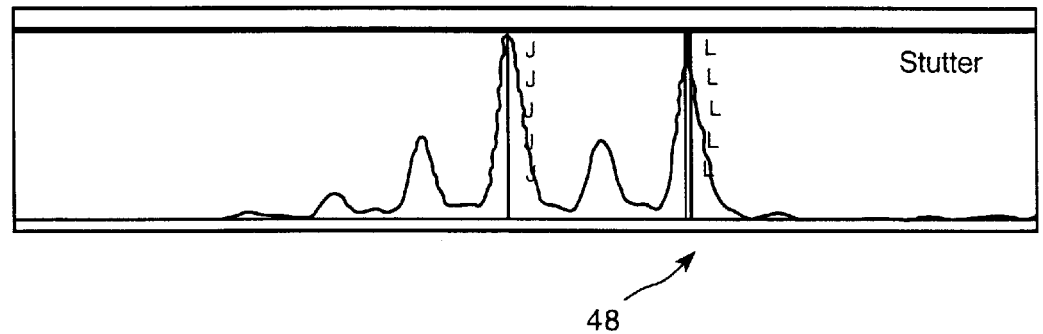

For stutter peaks, as shown in FIG. 5C, a model shape is formed from pre-existing alleles that exhibited stutter. If stutter is present it is part of the normal morphology of the marker so it will be present in the existing calls.

Figure 5D:
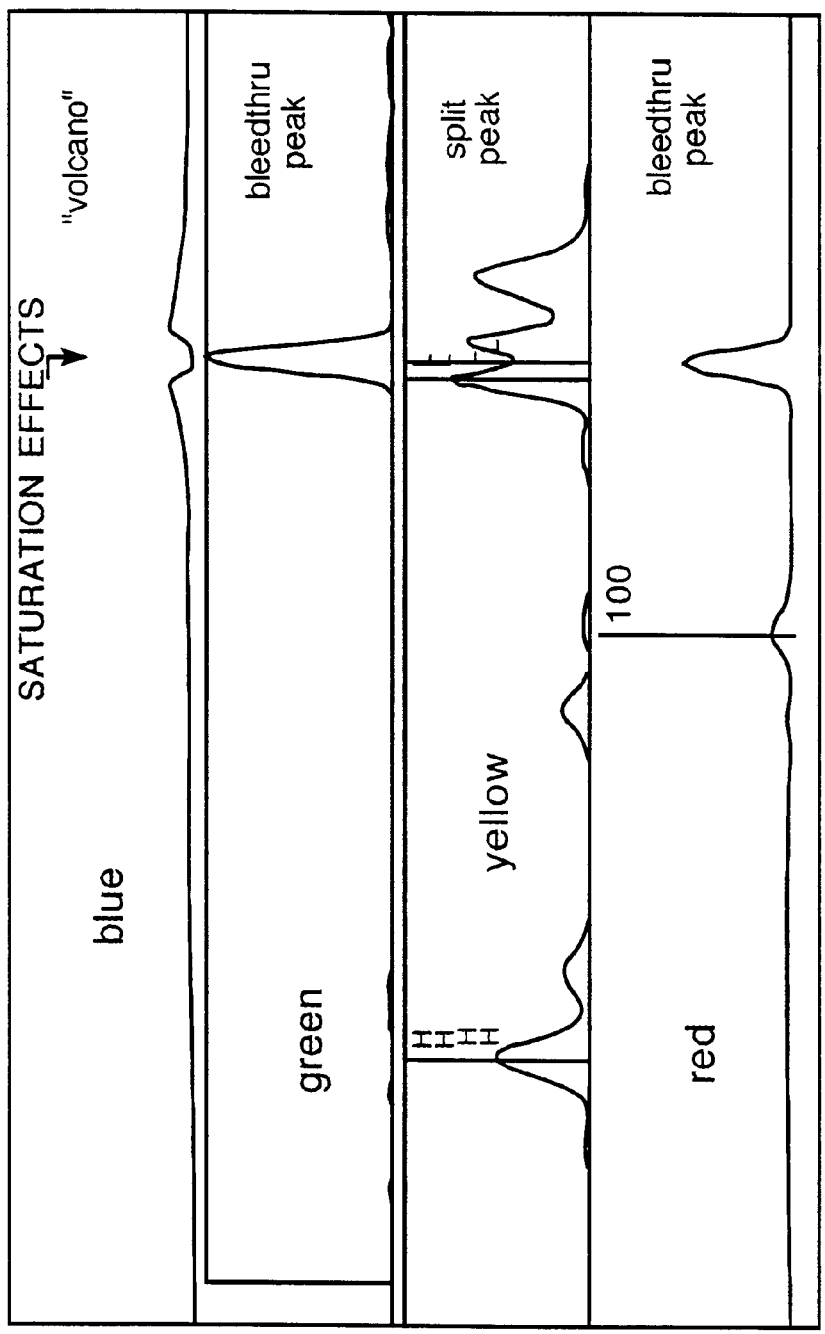
Figure 5E:
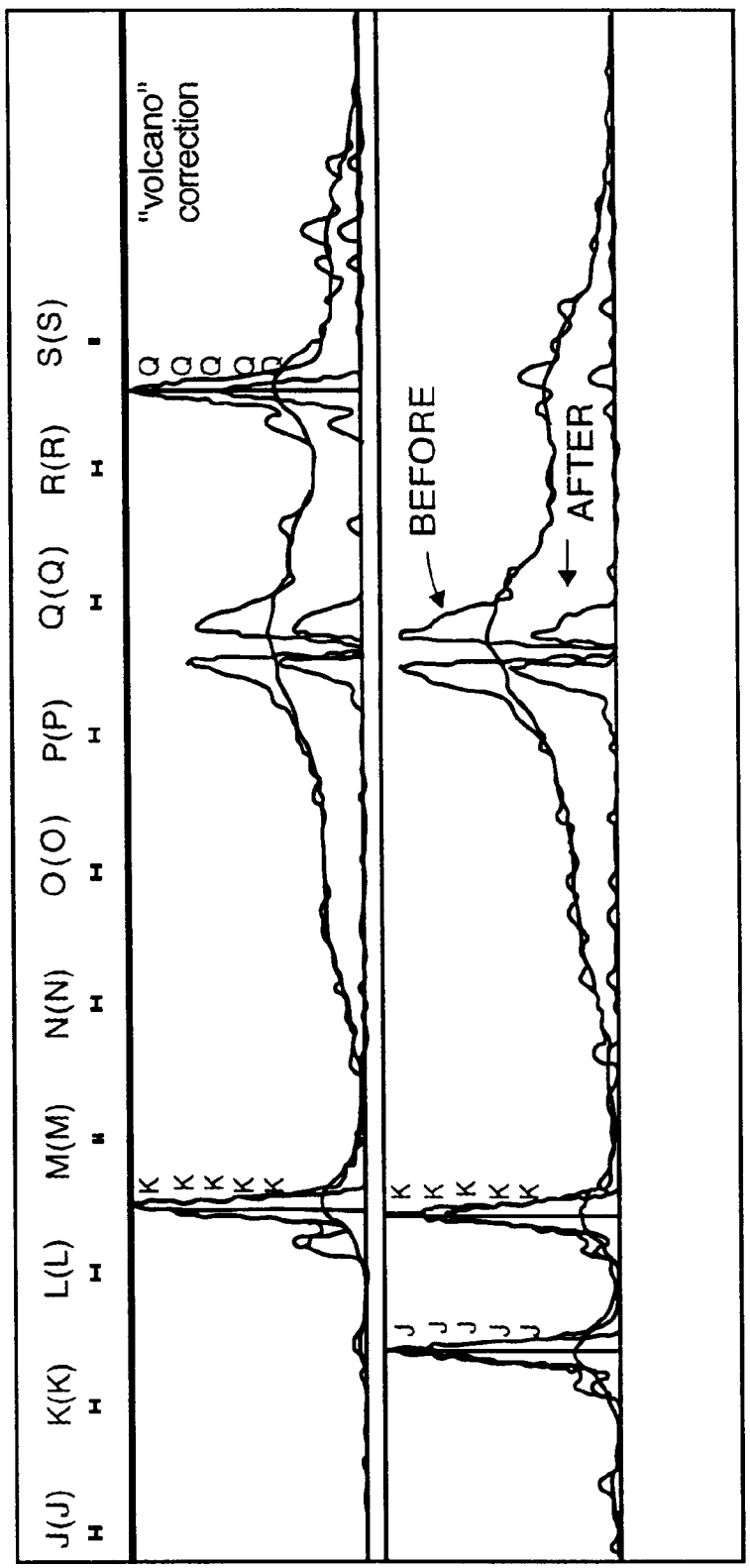

Referring briefly to FIGS. 5D and 5E, volcano and saturation effects in the trace data are shown. Volcano correction is part of the preprocessing. The split peak correction process is a saturation correction process. Saturation can also cause bleedthrough which was discussed above.

Figure 6A:
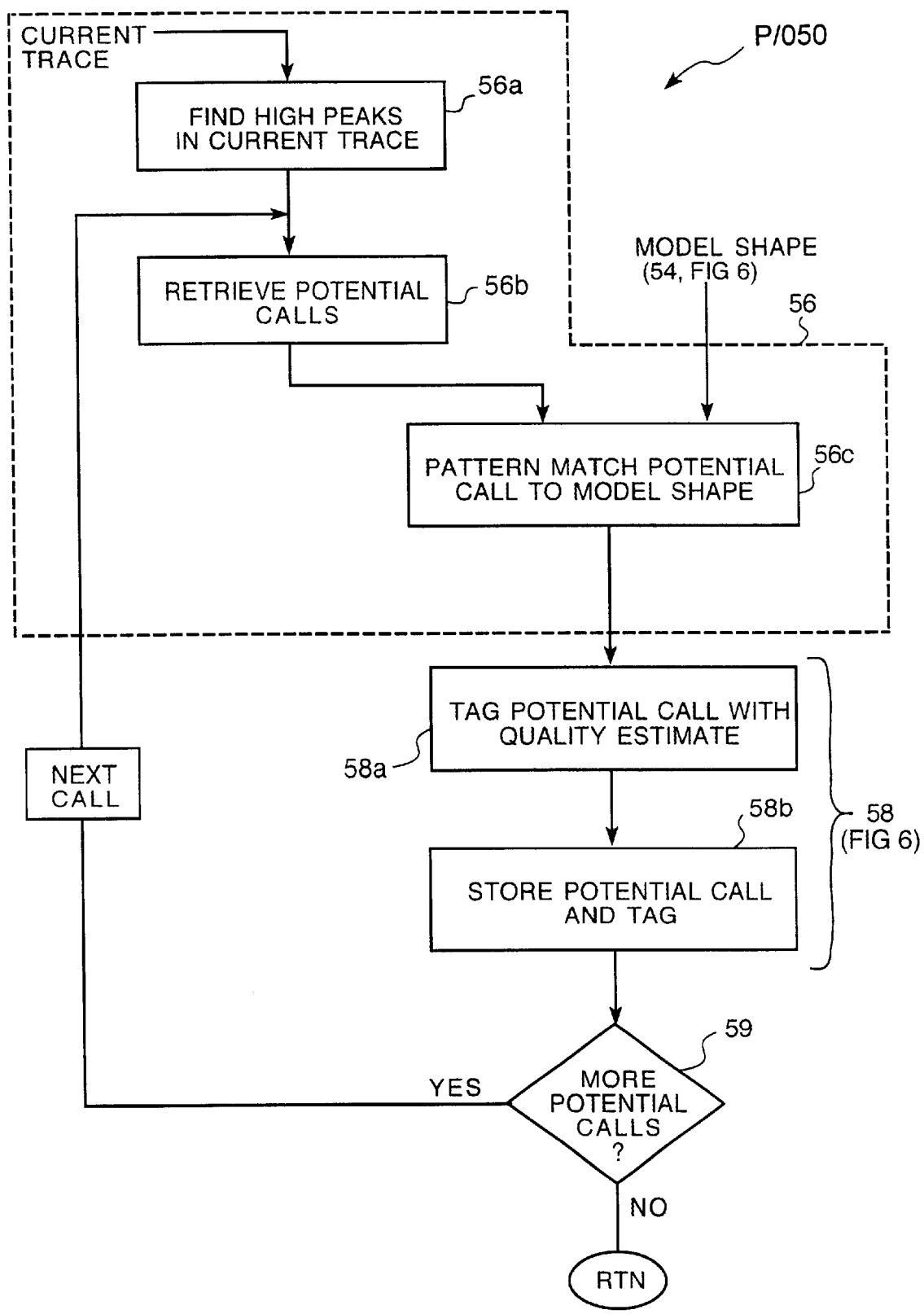
FIG. 6A is a flow chart of details of the model based allele caller of FIG. 6.

Referring now to FIG. 6A, details of the compare process 56 of the auto allele caller 50 are shown. The compare process 56 finds 56a all of the high amplitude peaks in a trace and generates potential calls. These potential calls are examined by the allele caller 50. The compare process 52 can have a process to retrieve 56b a potential call from the potential calls found 56a in the current trace. A pattern matcher 56b matches the retrieved potential call to the model or typical shape (from 54 FIG. 6). The model shape can be adjusted or corrected for each potential call, as will be described in FIG. 6B.

The reasonableness or quality estimate of the match is determined 58 for the potential allele call after the model shape has been matched to the retrieved call. The call is tagged with the result of determining the quality estimate. The process stores 56b the potential call and the tags. The auto allele caller 50 determines 59 if all of the potential calls in the trace have been examined. If all of the potential calls have been examined, the auto allele caller 50 exits; otherwise, the auto allele caller 50 retrieves the next potential call 60 and performs the pattern match 56c, correction, 57 tagging 58a, and storing 58b processes over a subsequent potential call.

Figure 6B:
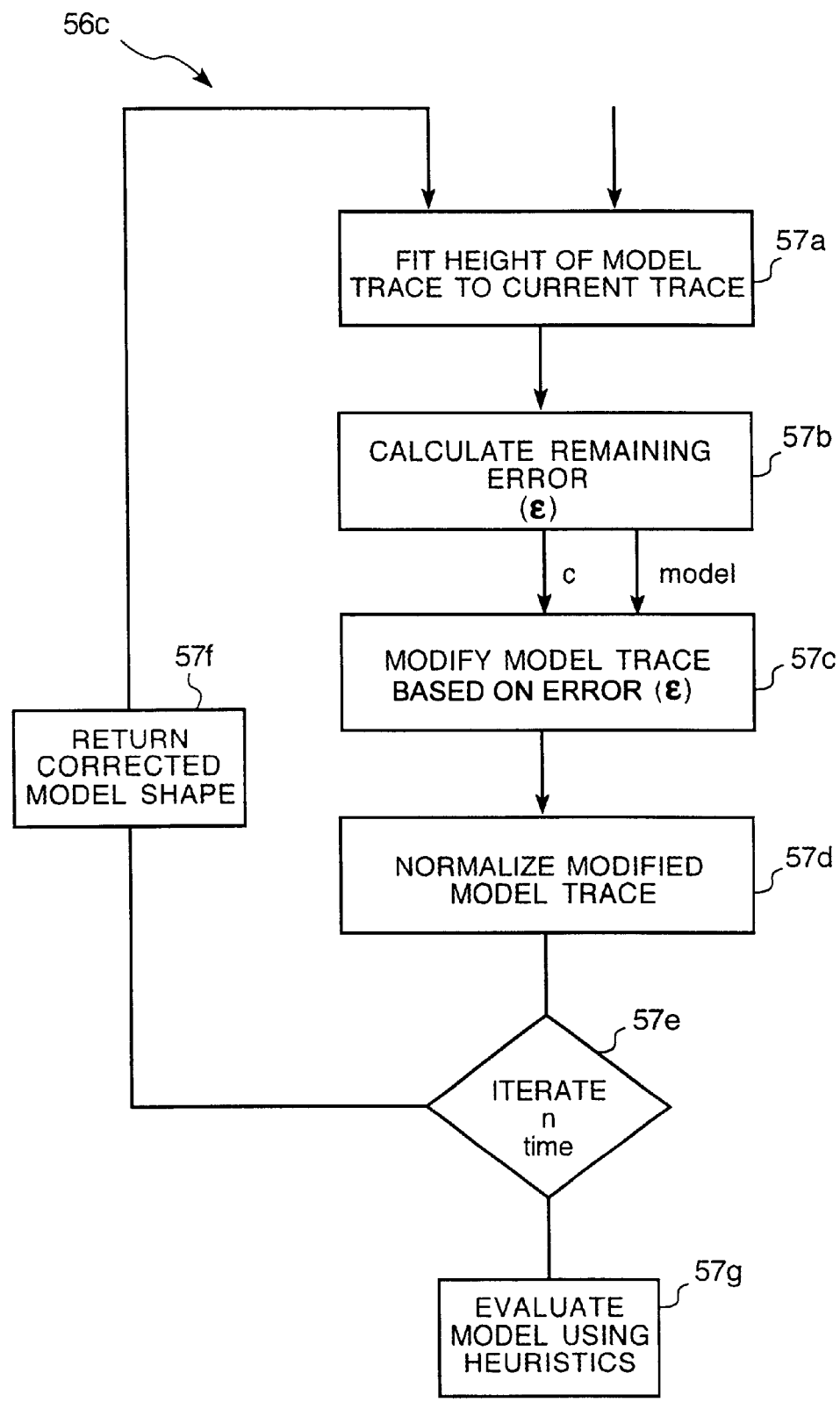
FIG. 6B is a flow chart showing a model correction process for the model based auto allele caller of FIG. 6.

Referring now to FIG. 6B, a model adjustment process is shown. The current trace data are used to correct the height of the model or typical shape (τ') by fitting the height of the model to the height of the current trace. The model trace is overlaid on possible genotypes and fitted 57a to a best height value. The fitted model is compared to the current trace to calculate 576 a remaining error factor (ε). The remaining error (ε), i.e., the difference between the height of the trace and the height of the fitted model is a vector quantity, i.e., one value per sample. The remaining error ε is used to further adapt or modify 57c the model trace. The typical error-corrected allele is given in Equation 6:

$$\vec{\tau}(t+1) = \vec{\tau}(t) \sum_{a \in alleles} \lambda \cdot \vec{\epsilon}_a(t) \tag{6}$$

where $\vec{\tau}$ is the typical allele, t is the iteration step, and $\vec{\epsilon}_a$ is the error for allele a in the possible genotype.

The corrected model trace is normalized 57d to have a maximum value of 1, to provide the model or typical allele for a subsequent iteration of the correction process 56. The process 56c will iteratively tune the typical allele shape for a single example. The process will apply a set of heuristic rules to the final tuned shape to evaluate the quality of the model.

The model-based allele caller 50 takes two sample traces f(s) and ($\vec{\tau}$) as input and attempts to call an allele. After baseline subtraction, an experimental process produces an output trace:

$$f(s) = c_1 a(s-s_1) + c_2 a(s-s_2) + \eta \tag{7}$$

where η is noise. A goal of allele calling is to determine the correct values of $s_1$, and $s_2$ given the trace signal f(s) where $s_1$ and $s_2$ are the allele positions.

In equation (7), $c_1$ and $c_2$ are unknowns and ($\vec{\tau}$), the typical allele shape, is an approximation to a(s), where both f(s), a(s) and $\vec{\tau}$ are zero outside a restricted range of values.

Given f(s) and a set of pairs ($s_1$, $s_2$) that includes all reasonable candidates, the correct call for that trace can be generated. Similarly, given the trace along with (τ') and a candidate pair ($s_1$, $s_2$), approximations $<c_1>$ and $<c_2>$ to coefficients $c_1$, $c_2$ can be computed using standard linear algebra.

Production genotyping produces a series of data sets, (i.e., one for each genetic marker and family collection). Each data set includes dozens to hundreds of traces f(s) that can be processed using a single approximation (τ'). Because a(s) varies from trace to trace even within a data set, process 50 starts with a generalized model of the average allele shape (τ') for the marker and specializes the model to best fit each individual training example.

The model is initialized with the generalized model of allele shapes τ'. The input I(s) has weights given by equation (9).

$$I(s) = \begin{cases} (c_1) & \text{if } s = s_1, \\ (c_2) & \text{if } s = s_2, \text{ and} \\ 0 & \text{otherwise} \end{cases} \qquad \text{Equation (9)}$$

The model-based auto allele caller 50 is set up to compute an approximation $<f>(s)$ according to Equation 8 above, with weight constraints equalizing the weights of $s_1$, and $s_2$. The inputs $<c_1>_i$ and $<c_2>_i$ are approximated at each iteration, I, using linear algebra, and the weights are updated using f(s), as a target output.

The typical allele adjustment process addresses the problem of iteratively tuning the approximations $(c_1)_i$, $(c_2)_i$, and $a(s)_i$ to best fit a single example f(s) for a single candidate for ($s_1$, $s_2$).

After iteratively tuning the typical allele shape for a single example, (which may require only about 20 iterations), the set of heuristic rules are applied to evaluate the quality of the final approximation $\vec{\tau}_n$.

These rules compare the initial to the final approximation to determine whether the observed impulse response (i.e., shape of the adjusted typical allele) $\vec{\tau}_n$ is a plausible variant of the expected impulse response a(s) which corresponds to the initial typical allele for the marker and information concerning properties of all plausible allele shapes. The heuristic rules include:

1. The highest stutter peak should fall at (called peak—repeat size).
2. Is the stutter height close to original?
3. Is the called peak height close to original?
4. Are there high peaks at BP sizes greater than called peak.

The candidate pairs $(s_1, s_2)$ are ranked according to a quality metric that combines overall error statistics with the heuristic plausibility measures or rules mentioned above. The top ranking candidate alleles are output from the allele calling module 50 and additional heuristics rules can be applied to remove candidate alleles that are identified as bleedthrough or other problematic peaks. The metrics include:

1. Penalize high remaining error after adaptation.
2. Penalize large differences in peak height.
3. Penalize adapted typicals that do poorly on heuristic rules.

Figure 7:
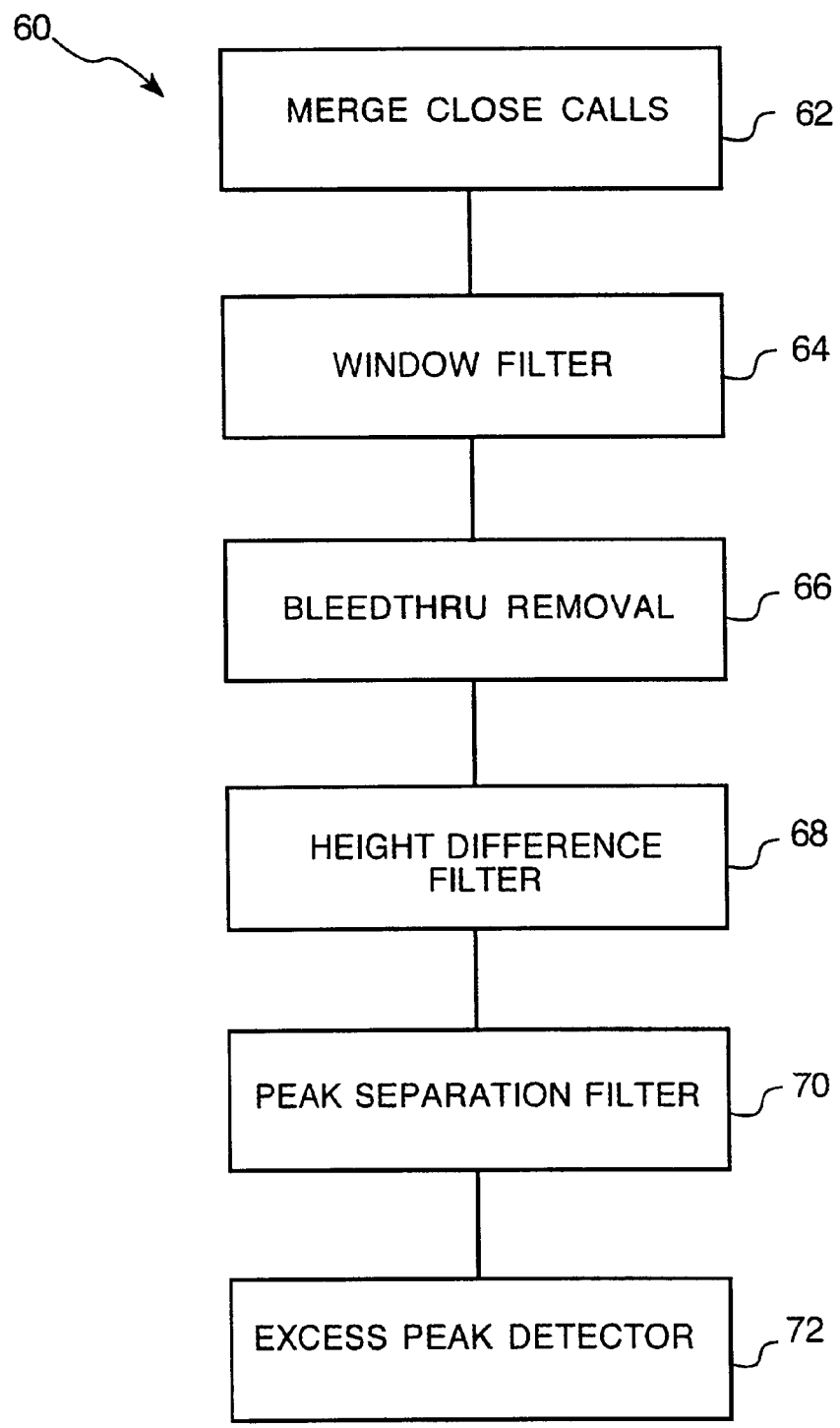
FIG. 7 is a flow chart showing post-processing of called alleles.

Referring now to FIG. 7, additional heuristics are applied to the output from the auto allele caller module 50. The heuristics include a "merge_close_calls_routine" 62 which filters peaks that are within a predetermined number of base pairs in distance. Thus, for example, a threshold value of about 1.0 preferably 0.5, and more preferably 0.25, base pairs or less can be used to filter adjacent peaks. Thus, if two candidate alleles are close together (i.e., within the ranges mentioned above) the lower of the two candidate alleles is discarded.

A window filter 64 can also be applied to the candidate alleles to discard peaks having a height outside a specified range. That is, the window filter would consider peaks that fall within the dynamic range of the system 10. A lower threshold of the window filter would be based upon the inherent noise characteristic of the system, whereas, an upper threshold would be based upon a saturation characteristic of the system. Bleedthrough detection 66 can also be applied to the outputs. Thus, the bleedthrough detection 66 can detect a bleedthrough condition and discard peaks that exhibit bleedthrough. Alternatively, if the processing of FIG. 3B were used, this bleedthrough detection 66 could be eliminated since the bleedthrough correction (43, FIG. 3B) is applied to the trace data to correct peaks that exhibit bleedthrough.

Figure 9:
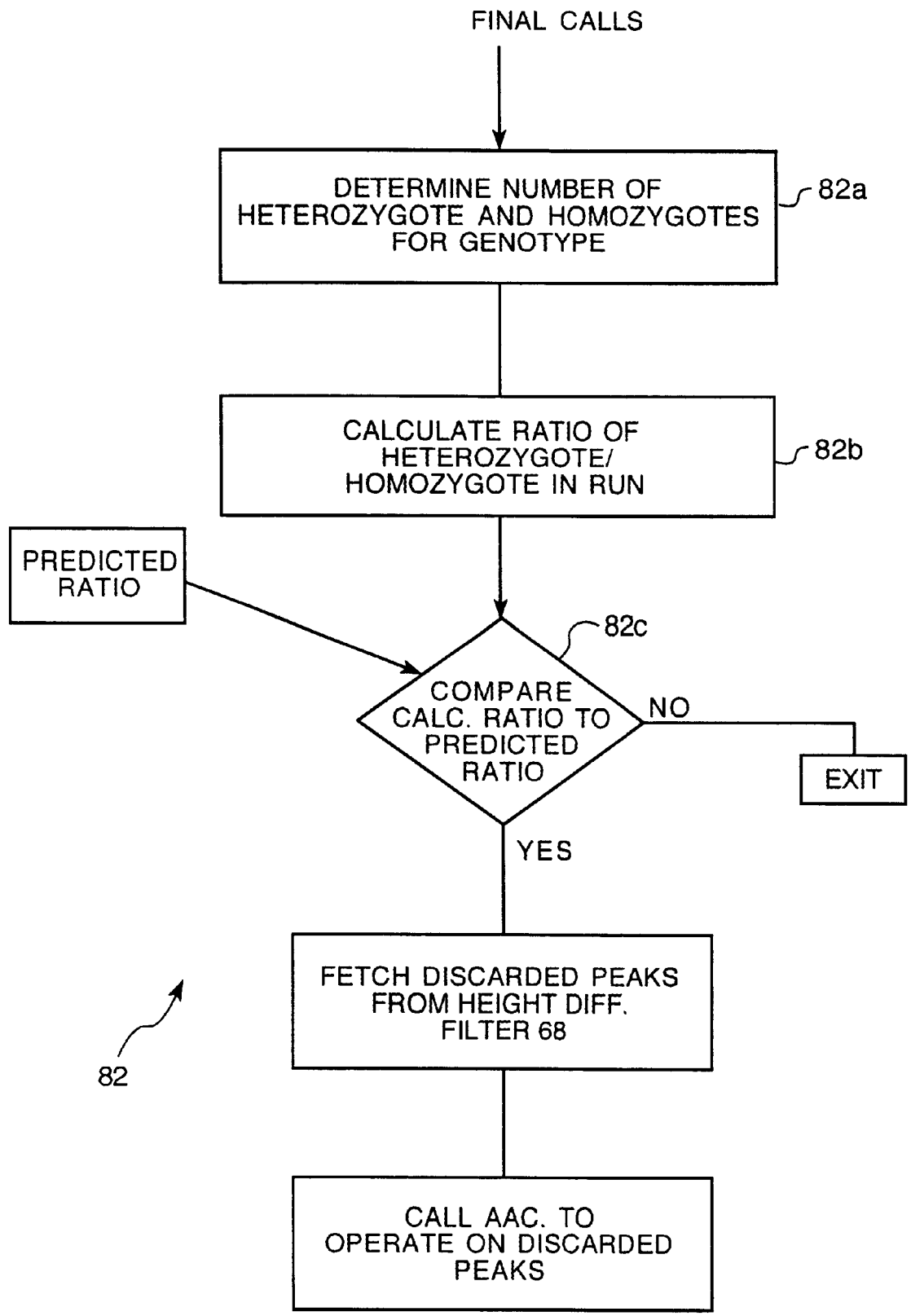
FIG. 9 is a flow chart showing details of an equalization process used in the shorty-allele detection of FIG. 8.

Additional heuristics that can be applied to the trace data include a height difference filter 68 that discards from further consideration those peaks that have a height less than a predetermined percentage of the height of the peak with the maximum height. A typical value for this filter is a peak height >0.18 of maximum peak. However, peaks which are removed from consideration may be so identified and returned for subsequent application to the auto allele caller 50 in response to a shorty-allele detection 80 (FIG. 9). Another heuristic is a peak separation filter 70 that examines if a pair of peaks are within a fraction of a repeat size. The filter 70 discards the peak having a lower magnitude if it is within a fraction of a repeat size (e.g., repeat size 0.83) of an adjacent peak. An excess peak detector 72 is used to discard multiple peaks (e.g., greater than 2) while retaining only the two peaks having the highest certainty or quality.

Figure 8:
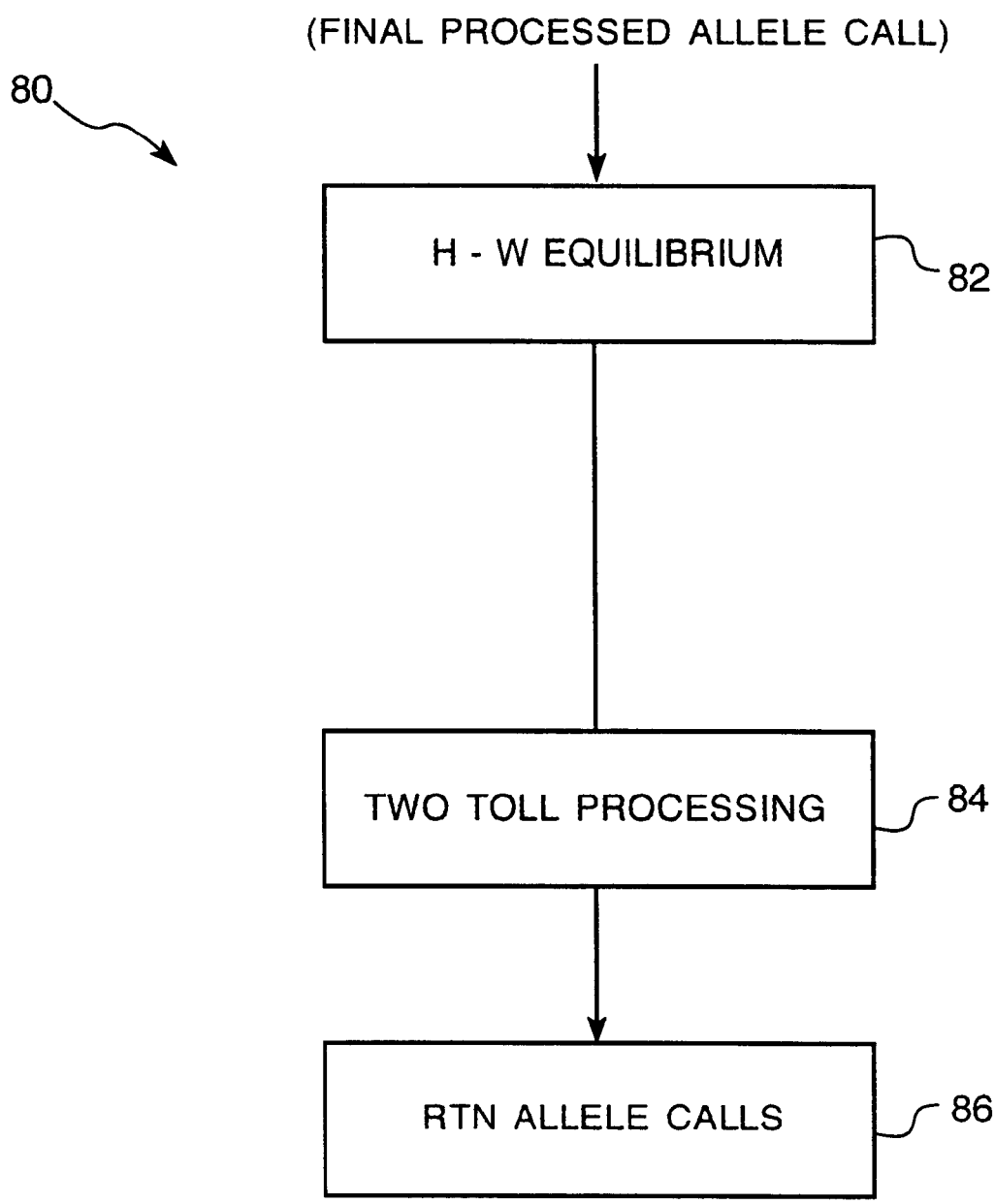
FIG. 8 is a flow chart showing a shorty-allele detection technique.

Referring now to FIG. 8, a so-called "shorty allele detection process" 80 is shown. This process 80 can be applied to all final calls from the output of the post detection heuristic processing 60. Shorty allele occurrence is common on tri- and tetranucleotide repeat markers but is not as prevalent on dinucleotide repeat markers. The shorty-allele detection process 80 can distinguish a shorty allele from noise or stutter. The shorty-allele detection process includes an H_W equilibrium process 82 and a two-tall process 84. The shorty-allele detection process will return 86 called alleles.

Referring now to FIG. 9, the H_W equilibrium detection process 82 is called once all of the other processing for a run has been completed. The H_W equilibrium process 82 determines 82a the number of heterozygotes and homozygotes that are identified for a given genotype. From the number of heterozygotes and homozygotes, the process calculates 82b a heterozygote to homozygote ratio. The process 82 will compare 82c the calculated heterozygote to homozygote ratio with a predicted heterozygote to homozygote ratio. According to the so-called Hardy-Weinberg Equilibrium Rule, in a given population, there should be a certain ratio of heterozygotes to homozygotes for any given genotype. If the comparison 82c indicates that the calculated ratio equals the predicted ratio (plus/minus an empirically determined tolerance) the process 82 will return a result that indicates that the process did not detect a shorty-allele. If, on the other hand, the comparison 82c indicates that the computed ratio does not equal the predicted ratio, the process 82 will fetch 82d discarded peaks from the height difference filter 68 (FIG. 7) and call the auto allele caller to operate on the discarded peaks. Thus, the H_W equilibrium process 82 may indicate that some of the peaks that were discarded in prior tests may have corresponded to a shorty-allele. For example, the height difference test discards peaks based on their height relative to another peak in the same trace. Thus, a shorty-allele in a heterozygote can be discarded by this test, whereas, a shorty-allele in a homozygote will be retained. This occurrence will cause a deviation in the calculated heterozygote/homozygote ratio from the predicted value of that ratio. If the shorty-allele process detects such a deviation, the shorty-allele process can return to the auto allele caller 28 and attempt to call one or more of the peaks that were discarded in the height difference filter 68. Other filters or processes that may do this include the allele caller 50.

It may be that after applying the shorty-allele detection process to the final allele calls, a hypothesized shorty-allele could occur in a trace that already has two tall alleles. The two talls process 84 will discard, the hypothesized shorty-allele, since only a maximum of two alleles per trace is possible.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method executed in a computer system for identifying potential alleles from a trace, the method comprising:

retrieving pre-existing allele calls for a marker, forming an allele shape by determining an average shape of the pre-existing allele calls to provide a allele shape for an allele at the marker, said allele shape characterized by a height and shape that is expected for identification of the allele at a known base pair marker;

applying the allele shape for an allele for the marker to the trace;

identifying potential allele calls that match to the shape of the allele at the marker;

assigning a quality factor to the potential allele calls; and rendering on an output device, an indication of whether portions of the trace correspond to alleles.

2. The method of claim 1, wherein forming the allele shape further comprises:

correcting the allele shape in accordance with the trace.

3. The method of claim 2, wherein correcting further comprises:

fitting the height of the allele shape to the height of the trace.

4. The method of claim 2, wherein correcting further comprises:

calculating an error factor associated with the allele shape based on the trace; and modifying the allele shape to minimize the error factor.

5. The method of claim 2, wherein correcting further comprises:

normalizing the allele shape to a value of one.

6. The method of claim 2, wherein correcting further comprises:

calculating an error factor associated with the allele shape based on the current trace data;

modifying the allele shape to minimize the error factor;

normalizing the trace; and fitting the height of the shape in accordance with the current trace data.

7. A method executed in a computer system for identifying alleles from a trace, the method comprising:

retrieving pre-existing allele calls based on a marker corresponding to the trace data;

forming from the pre-existing allele calls a shape for alleles at the marker;

comparing the trace to the shape to identify an allele; and rendering on an output device, an indication of portions of the trace correspond to the allele.

8. The method of claim 7, wherein comparing further comprises:

tagging the peaks with a quality estimate of the match; and storing the peaks and tags.

9. The method of claim 8, wherein tagging with a quality estimate is applied after the shape for alleles at the market has been corrected by applying the shape for alleles at the marker to the trace.

10. A method executed in a computer system for identifying alleles from trace data, the method comprising:

extracting trace data from a database;

preprocessing the trace data to correct for peak errors in the trace data;

comparing peaks in the trace data to an allele shape corresponding to an allele to produce at least one potential allele identification;

postprocessing the at least one potential allele identification by applying at least one heuristic processing criteria to the at least one potential allele identification to determine whether the at least one potential allele identification should be an allele call; and rendering on an output device, an indication of whether portions of the trace correspond to potential alleles.

11. The method of claim 10, wherein preprocessing comprises correcting for a split peak characteristic in the trace data.

12. The method of claim 10, wherein correcting for a split peak characteristic comprises:

finding a pair of peaks having maximum amplitudes within a predetermined distance of about two base pairs;

testing for bleedthrough to identify it as a split peak; and inverting a valley disposed between the pair of peaks.

13. The method of claim 10, wherein preprocessing further comprises correcting for a +A characteristic in the trace data.

14. The method of claim 13, wherein the +A correction further comprises:

detecting a +A characteristic in the trace data; and modifying the allele shape to include a +A peak after each primary peak in the allele shape.

15. The method of claim 10, wherein the preprocessing further comprises correcting for bleedthrough.

16. The method of claim 15, wherein correcting for bleedthrough comprises:

determining bleedthrough markers;

computing an average bleedthrough for all color combinations corresponding to trace data obtained from color lanes in an electrophoretic gel; and applying the average to the trace data to remove the bleedthrough.

17. The method of claim 10, wherein post heuristic processing comprises:

merging a pair of potential allele calls into a single potential allele call if the pair of potential allele calls are spatially separated by a distance less than a predetermined number of base pairs.

18. The method of claim 10, wherein postprocessing further comprises:

discarding potential alleles if the associated peak has a height below a noise threshold of the system or above a saturation threshold of the system.

19. The method of claim 10, wherein the postprocessing comprises detecting whether a bleedthrough occurred in the peaks and, if bleedthrough occurred, deleting the potential allele calls associated with those peaks.

20. The method of claim 10, wherein postprocessing comprises detecting whether the peaks associated with potential allele calls have a height difference within a predetermined value and discarding the potential allele calls whose associated peak has the lower height.

21. The method of claim 10 wherein comparing further comprises assigning an estimate of certainty to each potential allele call processed.

22. The method of claim 10, wherein postprocessing comprises:

determining if the peaks associated with a pair of adjacent potential allele calls each having a tag estimating certainty, are closer than a predetermined repeat size, and, if they are within the predetermined repeat size, discarding the potential allele having the lower estimate of certainty.

23. The method of claim 22, wherein determining for each potential genotype whether the genotype has more than two potential allele calls; and for those genotypes having more than two potential allele calls, discarding all subsequent alleles in excess of two alleles in accordance with the estimate of certainty associated with each allele.

24. A computer program product residing on a computer readable medium for identifying potential alleles from a trace, comprising instructions for causing a computer to:

retrieve pre-existing allele calls for a marker and forming a allele shape by forming an average shape of the pre-existing allele calls to provide the shape for an allele at the marker;

apply the allele shape for an allele for the marker to the trace;

identify potential allele calls that match to the shape of the allele at the marker;

assign a quality factor to the potential allele calls and render on an output device, an indication of whether portions of the trace correspond to potential alleles.

25. The computer program product of claim 24, wherein instructions that cause the computer to form the shape further comprise instructions that cause the computer to:

correct the allele shape in accordance with the trace.

26. The computer program product of claim 25, wherein instructions that cause the computer to correct further instructions that cause the computer to:

fit the height of the allele to the height of the trace.

27. The computer program product of claim 26, wherein instructions that cause the computer to correct further comprise instructions that cause the computer to:

calculating an error factor associated with the allele shape based on the trace; and modifying the shape to minimize the error factor.

28. A computer program product residing on a computer readable medium for identifying alleles from a trace, comprising instructions for causing a computer to:

extract trace data from a database;

preprocess the trace data to correct for errors in the trace data;

compare peaks in the trace data to an allele shape to find potential allele calls;

postprocess potential allele calls by applying at least one heuristic processing criterion to the at least one potential allele call to determine whether the at least one potential allele call should be an allele call; and render on an output device, an indication of whether portions of the trace correspond to alleles.

* * * * *